(12) United States Patent
Shemesh et al.

(10) Patent No.: US 6,846,302 B2
(45) Date of Patent: Jan. 25, 2005

(54) NEEDLE PROTECTOR DEVICE

(75) Inventors: Eli Shemesh, Ashdod (IL); Menahem Kraus, Rehovot (IL)

(73) Assignee: Teva Medical Ltd., Ashdod (IL)

( * ) Notice: Subject to any disclaimer, the term of this patent is extended or adjusted under 35 U.S.C. 154(b) by 123 days.

(21) Appl. No.: 10/334,071

(22) Filed: Dec. 31, 2002

(65) Prior Publication Data

US 2004/0127857 A1 Jul. 1, 2004

(51) Int. Cl.[7] .............................. A61M 5/00; A61M 5/32
(52) U.S. Cl. ...................... 604/110; 604/192; 128/919
(58) Field of Search ................................ 604/110, 187, 604/192, 197, 198, 218; 128/919

(56) References Cited

U.S. PATENT DOCUMENTS 6,030,366 A * 2/2000 Mitchell ..................... 604/192
6,319,233 B1 * 11/2001 Jansen et al. ............... 604/192
6,679,864 B2 * 1/2004 Gagnieux et al. ........... 604/198

* cited by examiner

*Primary Examiner*—Nicholas D. Lucchessi
*Assistant Examiner*—Mark K. Han
(74) *Attorney, Agent, or Firm*—David Klein; Dekel Patent Ltd.

(57) ABSTRACT

A needle protector device comprising a protector tube slidingly disposed in an outer tube and slidingly disposed over a syringe comprising a needle, the protector tube comprising at least one abutment initially in engagement with the outer tube such that the protector tube is constrained from moving distally with respect to the syringe, a biasing device disposed inside the outer tube operative to provide an urging force on the protector tube in a direction that tends to urge the protector tube distally towards a tip of the needle, and a release mechanism operative to move the at least one abutment out of engagement with the outer tube upon distal pushing of a plunger of the syringe, such that when the at least one abutment is out of engagement with the outer tube, the biasing device urges the protector tube distally towards the tip of the needle.

8 Claims, 16 Drawing Sheets

NEEDLE PROTECTOR DEVICE

FIELD OF THE INVENTION

The present invention relates to devices that cover medical needles and sharps, such as to protect against accidental puncture and contamination.

BACKGROUND OF THE INVENTION

Pointed hollow needles are widely employed to puncture the skin of a person, especially to perform venipuncture for many purposes, such as but not limited to, injecting fluids and drugs directly into the bloodstream of patients. For example, a syringe, such as a pre-filled self-injection syringe, may contain medication that may be injected into the person through a needle attached to the distal end of the syringe.

Administering fluids to patients through venipunctures has been subject to serious problems of accidental puncture and contamination. Upon forming the venipuncture, the needle may be exposed to infectious agents, such as but not limited to, a patient infected with Acquired Immune Deficiency Syndrome (AIDS) or hepatitis. This may present a danger or hazard to relatives or clinical personnel who may inadvertently or accidentally jab or stick themselves with the used needle after withdrawal from the body of the person, with the possibility of infection or even death resulting therefrom.

Numerous prior art devices have been proposed for protecting relatives or clinical personnel from harm caused by accidental injuries through sticking themselves with needles withdrawn from the bodies of patients. For example, U.S. Patent Application No. 20020161337 to Shaw et al. describes an automatically operable safety shield system for use with a syringe. The safety shield system includes an inner holder having proximal and distal portions and defining an enclosure into which the syringe may be inserted. An outer shield having proximal and distal portions is mounted outwards from the inner holder and is axially movable relative to the inner holder between retracted and extended positions. A spring is positioned between a first detent on the inner holder and a second detent on the outer shield, and urges the outer shield to its extended position. The outer shield has a stop member that engages with an opening formed on the inner holder when the outer shield is in the retracted position. A trigger is positioned within the inner holder and axially movable relative to the inner holder such that it can contact the stop member when it is engaged with the opening on the inner holder and disengage the stop member from the opening, thereby allowing the spring to move the outer shield to the extended position and cover the needle tip.

However, Shaw et al. and the other known needle protecting devices may have drawbacks in terms of ease of use and manufacture.

SUMMARY OF THE INVENTION

The present invention seeks to provide an improved device that covers medical needles and sharps, which is easy to use and manufacture, as is described in detail hereinbelow. For example, in one embodiment of the invention, a needle protector is provided for use with a syringe, such as but not limited to, a pre-filled syringe. The contents of the syringe may be administered to a patient by piercing the patient's skin with a needle attached to the syringe, and then injecting all or some of the contents of the syringe into the patient by pushing a plunger slidingly disposed in the syringe. Pushing the plunger to administer the substance contained in the syringe automatically triggers a biasing device to urge the needle protector distally, whereupon the needle protector safely covers the needle tip upon removal of the needle from the patient's skin.

There is thus provided in accordance with an embodiment of the present invention a needle protector device comprising a protector tube slidingly disposed in an outer tube and slidingly disposed over a syringe comprising a needle, the protector tube comprising at least one abutment initially in engagement with the outer tube such that the protector tube is constrained from moving distally with respect to the syringe, a biasing device disposed inside the outer tube operative to provide an urging force on the protector tube in a direction that tends to urge the protector tube distally towards a tip of the needle, and a release mechanism operative to move the at least one abutment out of engagement with the outer tube upon distal pushing of a plunger of the syringe, such that when the at least one abutment is out of engagement with the outer tube, the biasing device urges the protector tube distally towards the tip of the needle.

In accordance with an embodiment of the present invention the at least one abutment comprises at least one resilient tongue that tends to spring radially outwards from an outer contour of the protector tube.

Further in accordance with an embodiment of the present invention the protector tube is formed with an elongate axial groove and a depression formed proximal to the groove, and the outer tube is formed with an elongate axial groove and a depression formed proximal to the groove, and at least one resilient tongue formed at a distal end thereof comprising lugs, wherein a proximal end of the at least one resilient tongue of the protector tube is initially fixedly received in the depression of the outer tube, and the lugs are initially received in the axial groove of the protector tube. The depression of the protector tube may be axially aligned with the groove of the protector tube. The axial groove and the depression of the protector tube may be formed through a wall thickness of the protector tube. The axial groove of the protector tube may be formed with a chamfered, proximal ramp. Additionally, the depression of the outer tube may be axially aligned with the groove of the outer tube, and the axial groove and the depression of the outer tube may be formed through a wall thickness of the outer tube.

Still further in accordance with an embodiment of the present invention the release mechanism comprises a ring with proximally extending syringe interface members and distally extending fingers.

In accordance with an embodiment of the present invention the at least one abutment comprises at least one outer ear initially proximal to at least one retaining stub formed in the outer tube, the at least one retaining stub configured to yield to distal pushing of the at least one outer ear thereagainst.

Further in accordance with an embodiment of the present invention the biasing device is not initially in a contracted state, and the release mechanism contracts the biasing device upon distal pushing of the plunger of the syringe.

Still further in accordance with an embodiment of the present invention the release mechanism comprises transverse ears arranged to lock on to a portion of the outer tube upon sufficient distal pushing of the plunger of the syringe so as to arrest movement of the release mechanism.

In accordance with an embodiment of the present invention a cap member is provided that receives therein a head of the plunger of the syringe, the cap member being arranged to lock on to a portion of the outer tube upon sufficient distal pushing of the plunger of the syringe so as to arrest movement of the plunger.

In accordance with another embodiment of the present invention the biasing device is formed as an integral extension of the protector tube.

There is also provided in accordance with an embodiment of the present invention a needle protector device comprising a protector tube slidingly disposed over a syringe comprising a needle, the protector tube being initially constrained from moving distally with respect to the syringe, a biasing device operative to provide an urging force on the protector tube in a direction that tends to urge the protector tube distally towards a tip of the needle, and a release mechanism operative to release and permit movement of the protector tube upon distal pushing of a plunger of the syringe, such that when the protector tube is released, the biasing device urges the protector tube distally towards the tip of the needle and the biasing device does not move reach the tip of the needle.

BRIEF DESCRIPTION OF THE DRAWINGS

The present invention is herein described, by way of example only, with reference to the accompanying figures, wherein.

DETAILED DESCRIPTION OF THE PREFERRED EMBODIMENT

Figure 1A:
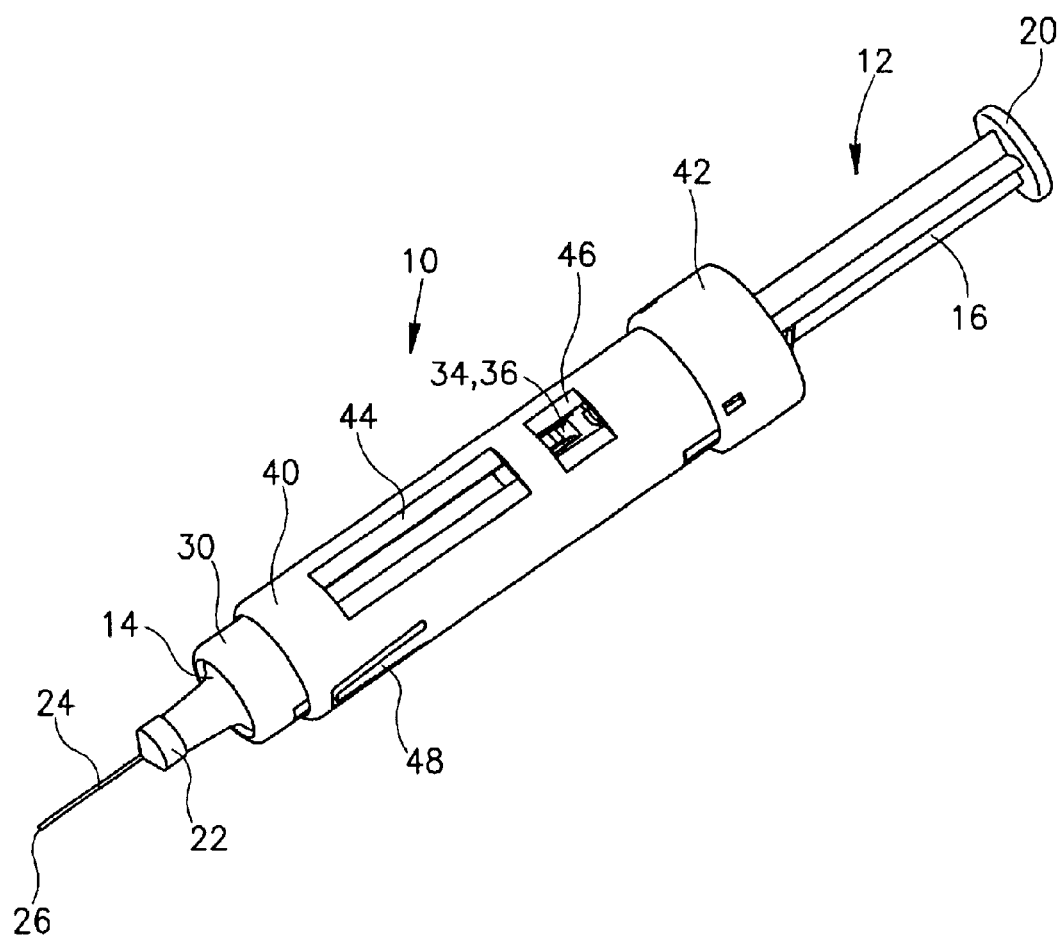
FIGS. 1A and 1B are simplified pictorial and sectional illustrations, respectively, of a needle protector device for use with a hypodermic needle assembly, constructed and operative in accordance with an embodiment of the present invention, wherein the needle protector device is in an initial retracted position that does not cover a needle tip of the hypodermic needle assembly.
Figure 1B:
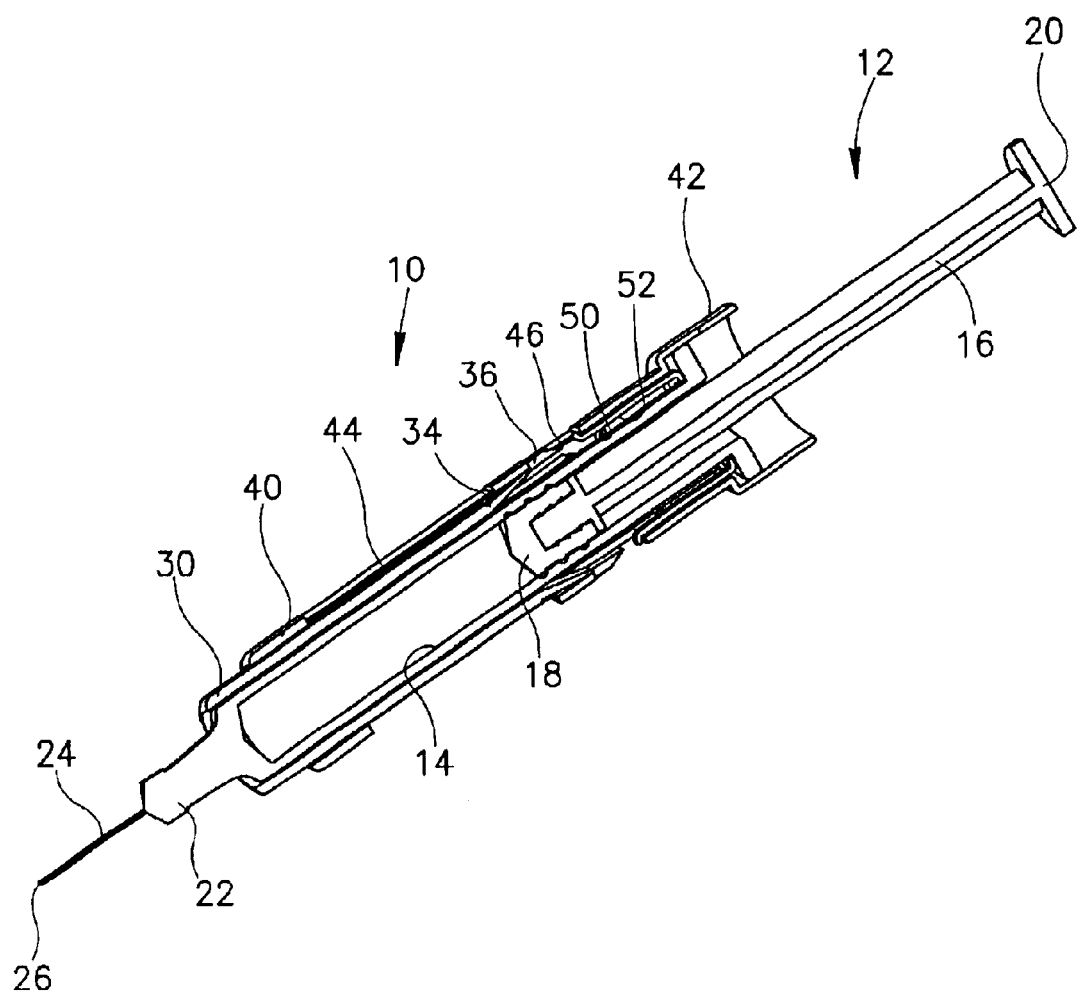

Reference is now made to FIGS. 1A and 1B, which illustrate a needle protector device 10 for use with a hypodermic needle assembly 12, constructed and operative in accordance with an embodiment of the present invention.

Hypodermic needle assembly 12 may comprise a syringe 14 in which is slidingly fitted a plunger 16. Plunger 16 comprises a distal elastomeric pusher 18 (FIG. 1B) and a proximal head 20. The distal (outlet) end of syringe 14 may be in fluid communication with a hub portion 22 of a needle 24 comprising a needle tip 26. As is well known in the art, the entire hypodermic needle assembly 12 and needle protector device 10 may be molded or otherwise constructed of a medically-approved plastic and provided to the end-user, e.g., the medical practitioner, in a sealed package (not shown), so that the assembly and device are in a completely sterile condition when removed from the package.

In accordance with an embodiment of the present invention, hypodermic needle assembly 12 is disposed inside needle protector device 10. Needle protector device 10 may comprise a protector tube 30, such as an inner hollow tube configured to slide over syringe 14. Protector tube 30 may be slidingly disposed in an outer hollow tube 40.

Figure 2:
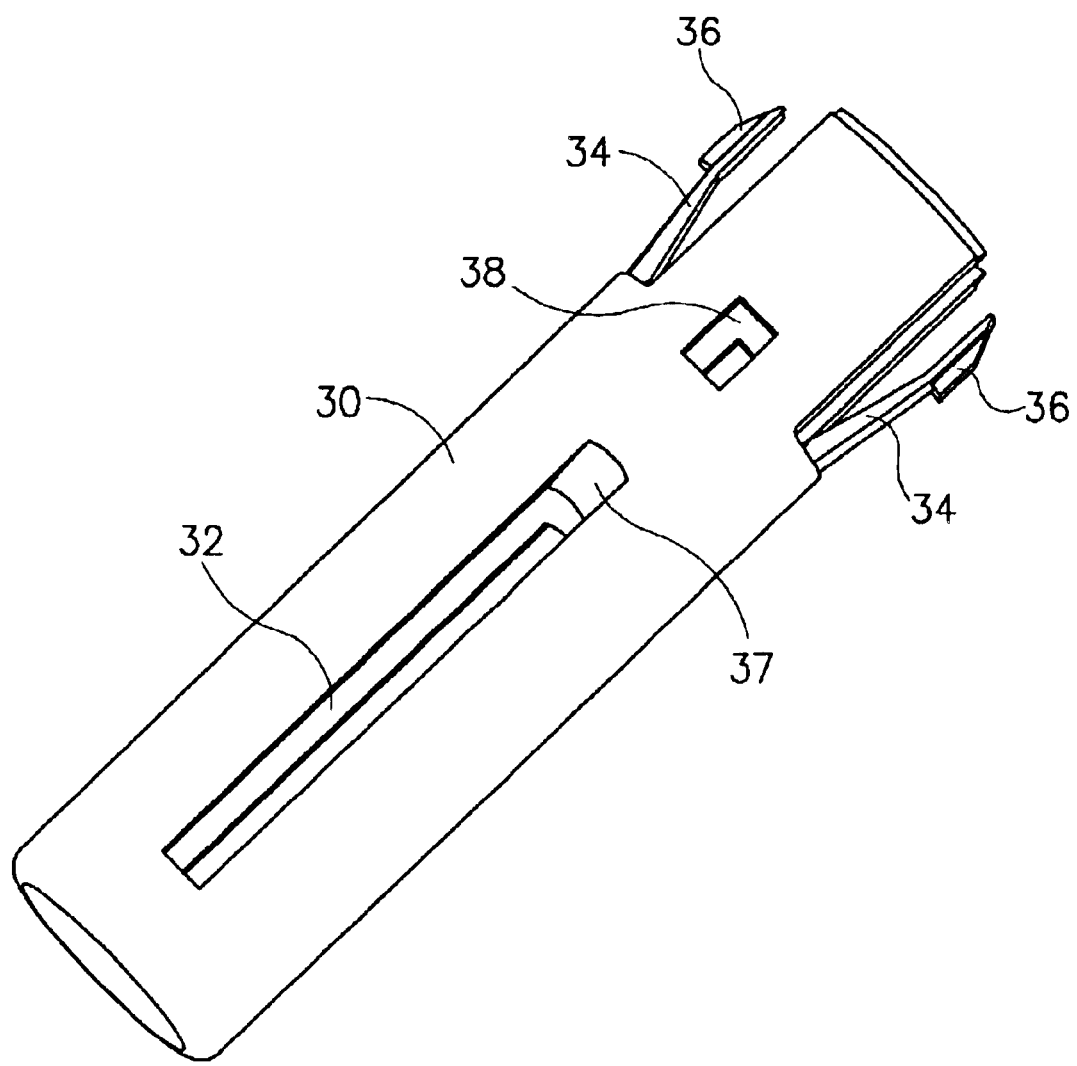
FIG. 2 is a simplified pictorial illustration of a protector tube of the needle protector device of FIGS. 1A and 1B, constructed and operative in accordance with an embodiment of the present invention.

Referring additionally to FIG. 2, protector tube 30 may comprise one or more abutments in the form of resilient tongues 34 at a proximal end thereof, which may be formed with outwardly chamfered proximal ends 36. Resilient tongues 34 tend to spring radially outwards from the outer contour of protector tube 30. Protector tube 30 may be formed with an elongate axial groove 32 and a depression 38 formed proximal to groove 32. Depression 38 may be axially aligned with groove 32. Axial groove 32 and depression 38 may be formed through the thickness of the wall of protector tube 30. Groove 32 may be formed with a chamfered, proximal ramp 37.

Figure 3:
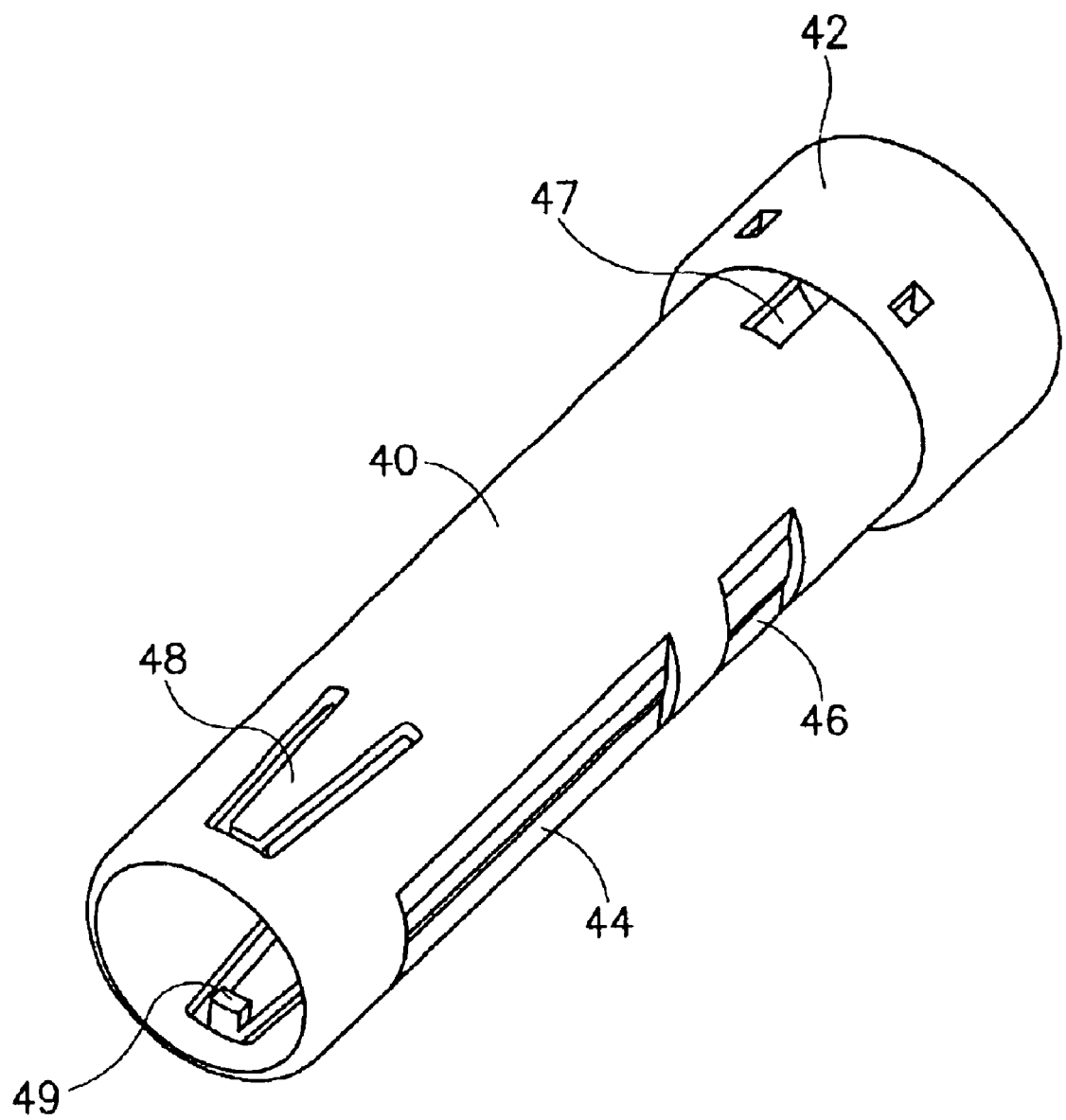
FIG. 3 is a simplified pictorial illustration of an outer tube of the needle protector device of FIGS. 1A and 1B, constructed and operative in accordance with an embodiment of the present invention.

Referring additionally to FIG. 3, outer tube 40 may comprise a proximal enlarged end 42, in which a proximal hub 17 of syringe 14 may be received (as seen in FIG. 1). Outer tube 40 may be formed with an elongate axial groove 44 and a depression 46 formed proximal to groove 44. Depression 46 may be axially aligned with groove 44. Axial groove 44 and depression 46 may be formed through the thickness of the wall of outer tube 40. One or more resilient tongues 48 may be formed at a distal end of outer tube 40, which may be formed with inwardly facing lugs 49. One or more channels 47 may be formed at a proximal end of outer tube 40 distally of enlarged end 42.

Figure 3A:
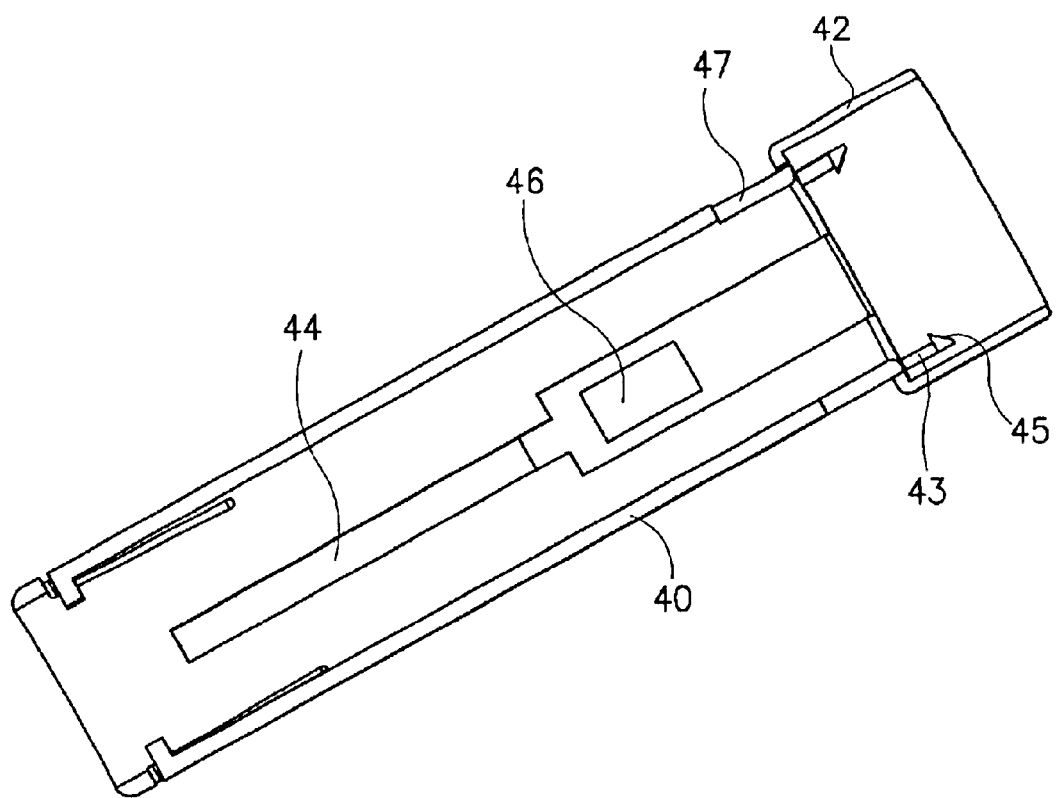
FIG. 3A is a simplified sectional illustration of an enlarged end of the outer tube of the needle protector device of FIGS. 1A and 1B, showing retaining members for fixedly holding a hub of a syringe of the hypodermic needle assembly, in accordance with an embodiment of the present invention.

Referring additionally to FIG. 3A, enlarged end 42 may comprise a plurality of inner, radially spaced, resilient retaining members 43, which may be formed with inwardly chamfered proximal ends 45. The proximal hub 17 of syringe 14 may be fixedly received and held by retaining members 43.

Figure 4:
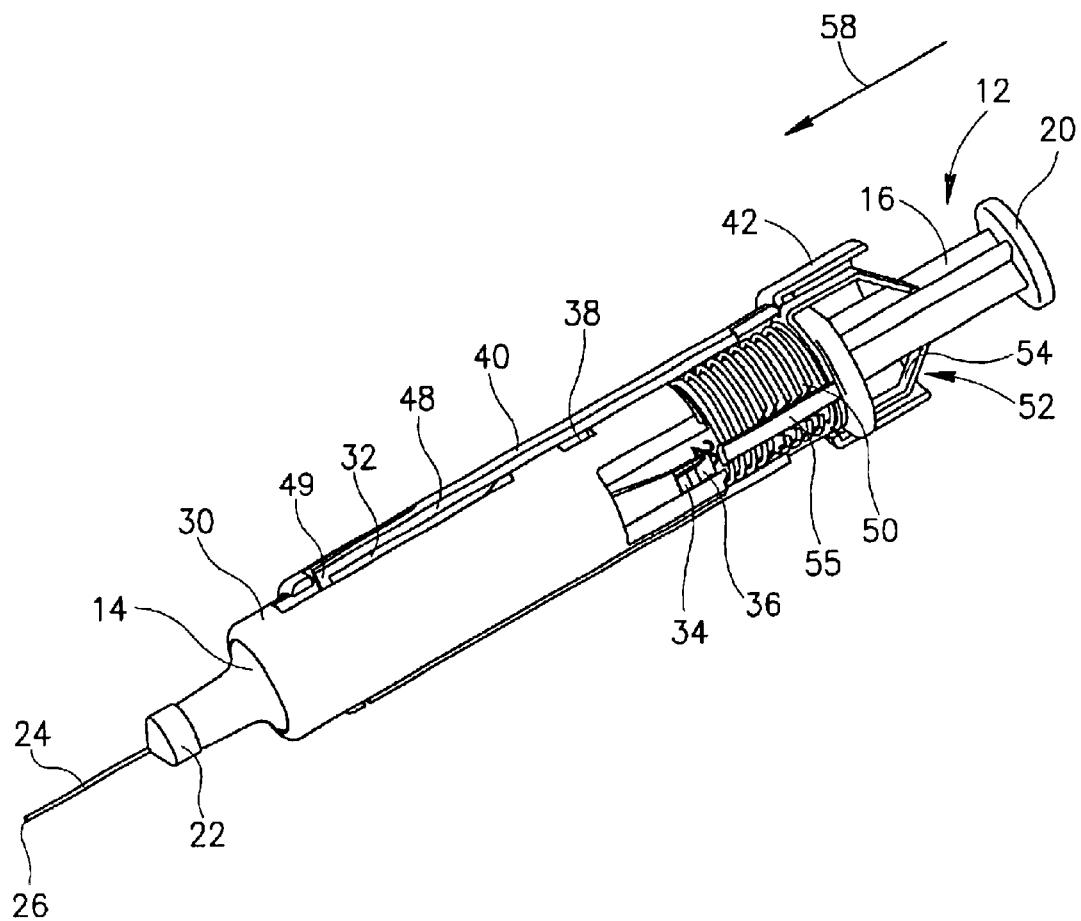
FIG. 4 is a simplified pictorial, partially cutaway illustration of the needle protector device of FIGS. 1A and 1B, showing a release mechanism constructed and operative in accordance with an embodiment of the present invention.

Referring additionally to FIG. 4, a biasing device 50, such as but not limited to, a coil spring, may be disposed inside outer tube 40 and provide an urging force on a proximal end of protector tube 30, which forces tends to urge protector tube 30 distally towards the needle end of hypodermic needle assembly 12. However, as seen best in FIGS. 1A and 1B, the proximal end 36 of tongue 34 is initially fixedly received in depression 46 of outer tube 40. In this position, protector tube 30 is prevented from being urge distally along syringe 14. It may be seen in FIG. 1A and FIG. 4 that lugs 49 are initially received in axial groove 32.

Figure 5:
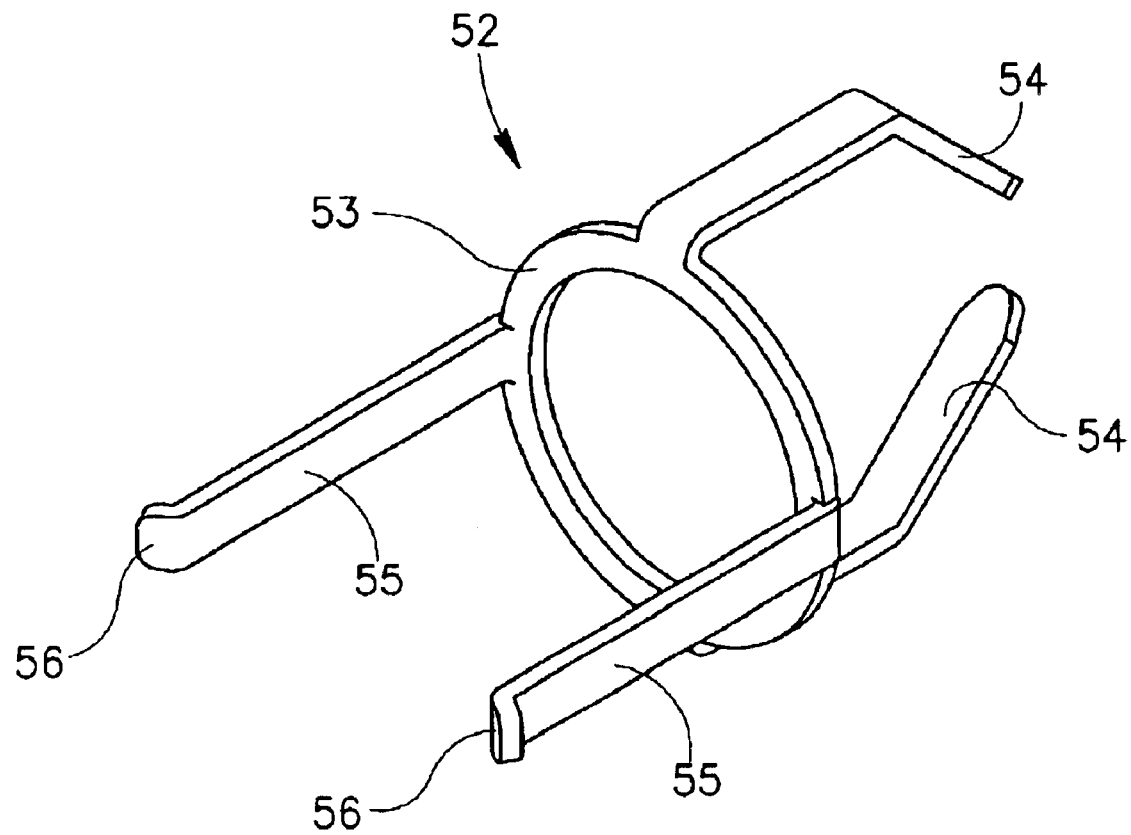
FIG. 5 is a more detailed illustration of the release mechanism shown in FIG. 4.

A release mechanism 52 may be disposed in outer tube 40. Release mechanism 52, shown in detail in FIG. 5 to which reference is now made, may comprise a ring 53 with proximally extending syringe interface members 54 and distally extending fingers 55. Fingers 55 may comprise bent ends 56, which may serve as chamfered surfaces to better push against ends 36 of tongues 34 of protector tube 30, as is described below. As seen in FIG. 4, syringe interface members 54 may sit in grooves of the shaft of plunger 16, and fingers 55 may initially not abut tongues 34 of protector tube 30. Release mechanism 52 may be made of any suitably sturdy material, such as but not limited to, stainless steel.

Figure 6:
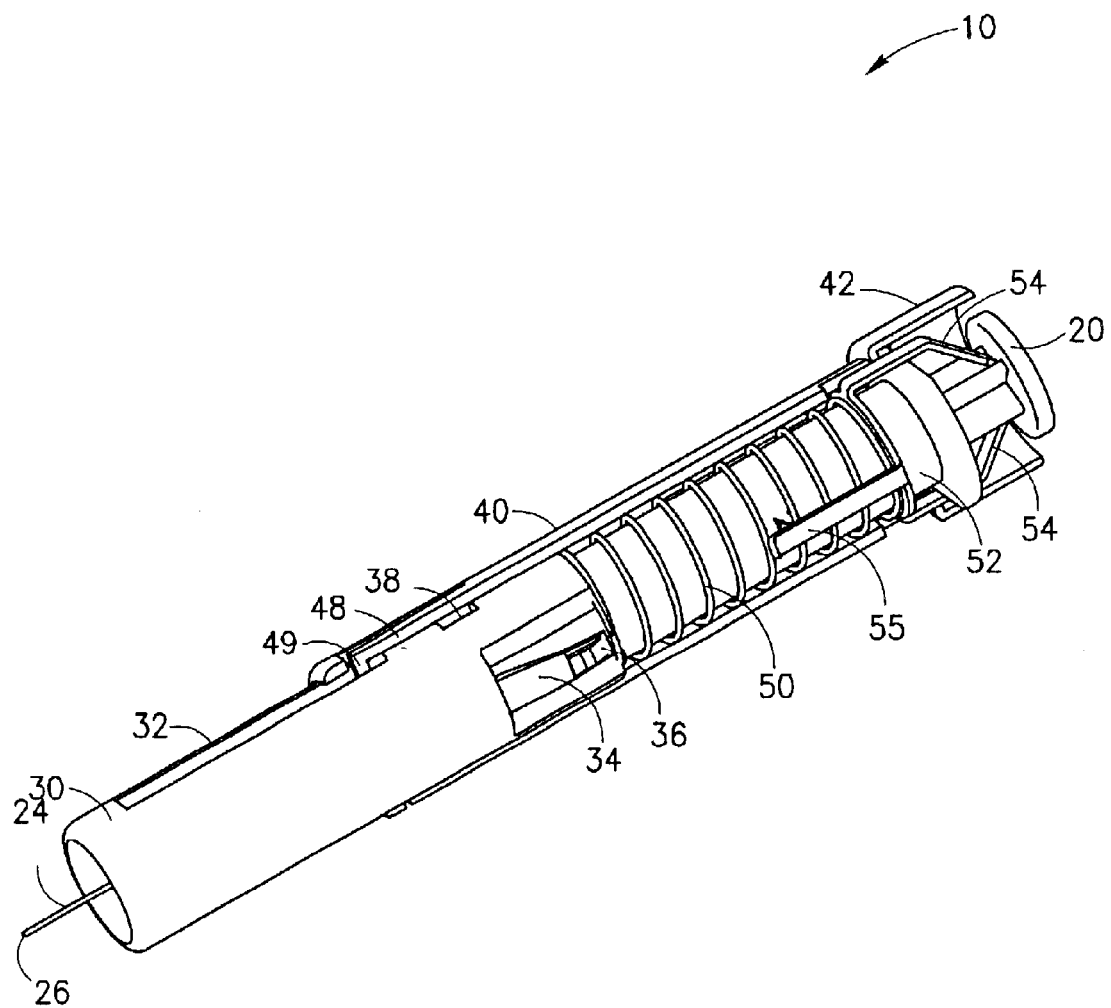
FIG. 6 is a simplified pictorial, partially cutaway illustration of the needle protector device of FIGS. 1A and 1B, after release of the protector tube by the release mechanism, but before covering the needle tip of the hypodermic needle assembly, in accordance with an embodiment of the present invention.

Plunger 16 may be pushed distally in the direction of an arrow 58 to inject fluid (not shown) from syringe 14 through needle 24. Upon further distal pushing of plunger 16 in the direction of arrow 58, head 20 of plunger 16 contacts and distally pushes syringe interface members 54 of release mechanism 52. This causes bent ends 56 (FIG. 5) of fingers 55 to slide over ends 36 of tongues 34 of protector tube 30, thereby radially pushing tongues 34 inwards and out of engagement with depressions 46 of outer tube 40. This permits biasing device 50 to urge protector tube 30 distally in the direction of arrow 58, as seen in FIG. 6. It is noted that channels 47 may permit unobstructed distal movement of release mechanism 52 with respect to outer tube 40.

In FIG. 6, protector tube 30 has moved distally towards covering needle tip 26, and is illustrated at a position where it may be stopped by the skin of a patient (not shown). Axial groove 32 has slid distally such that ramp 37 (at the proximal end of axial groove 32) is now adjacent lug 49 of outer tube 40.

Figure 7:
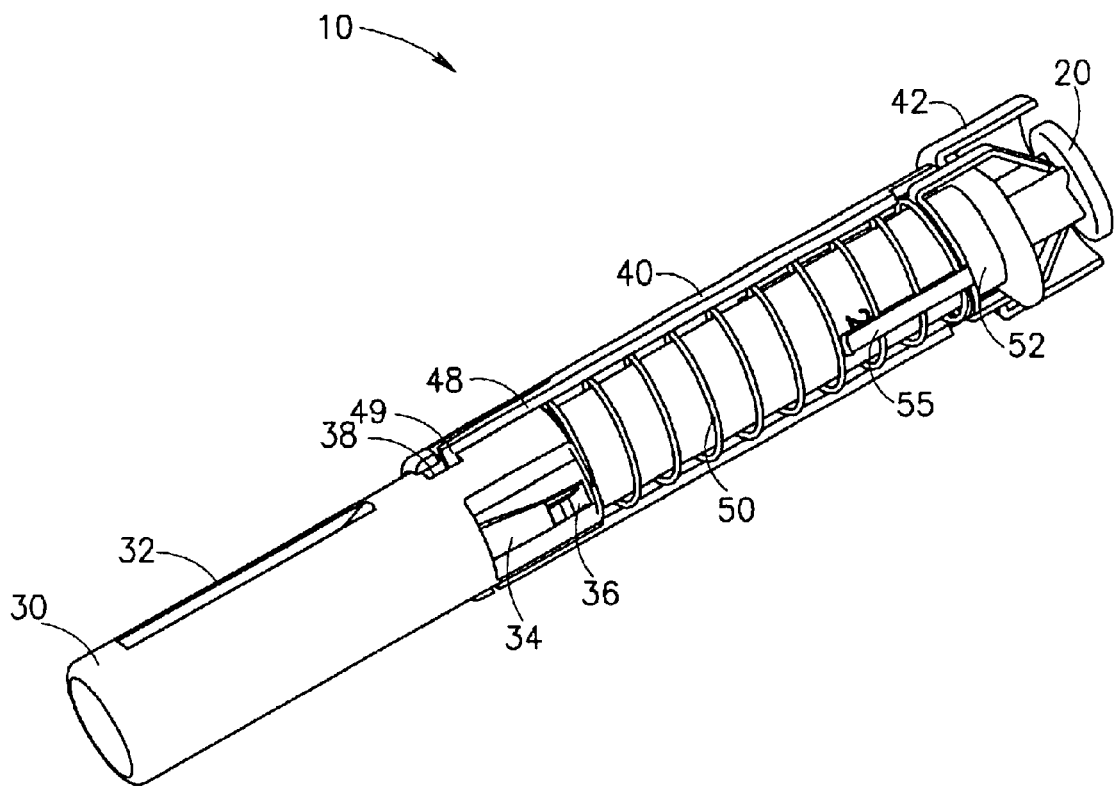
FIGS. 7 and 8 are simplified pictorial, partially cutaway and sectional illustrations, respectively, of the needle protector device of FIGS. 1A and 1B, after the protector tube has been urged distally to cover the needle tip of the hypodermic needle assembly, in accordance with an embodiment of the present invention.
Figure 8:
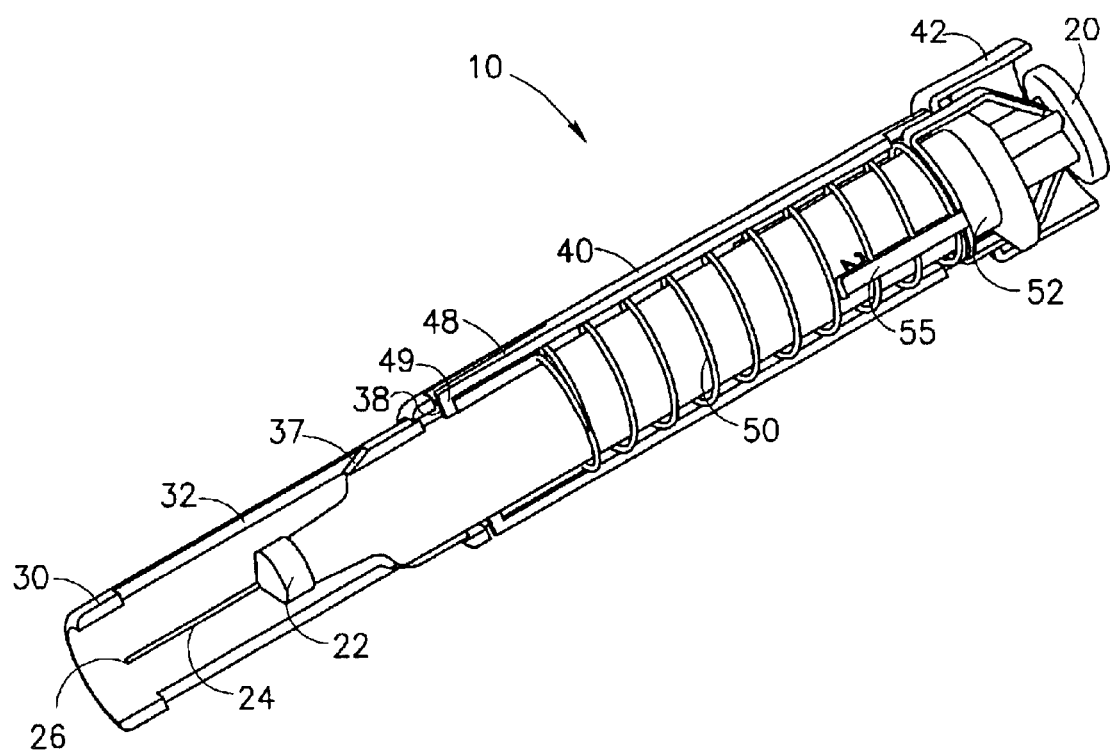

In FIGS. 7 and 8, protector tube 30 has continued to be urged distally and now covers needle tip 26. Ramp 37 has moved past lug 49 of outer tube 40, and lug 49 is now fixedly received in depression 38 of protector tube 30. This prevents further movement, both distally and proximally, of protector tube 30. Distal movement is also prevented by tongue 34 abutting the distal end of groove 44 and the syringe body. Thus, protector tube 30 protects against accidental or inadvertent pricking by needle tip 26.

Other variations of the above-described embodiment are possible within the scope of the present invention. One example is now described with reference to FIG. 9, which illustrates a needle protector device 60 for use with hypodermic needle assembly 12, constructed and operative in accordance with another embodiment of the present invention. Needle protector device 60 is similar in construction to needle protector device 10, with like elements being designated by like numerals. Needle protector device 60, unlike needle protector device 10, may comprise an elongate release mechanism 62, shown more in detail in FIG. 10. Release mechanism 62 may comprise a ring 63 with proximally extending syringe interface members 64 and distally extending fingers 65. Syringe interface members 64 may extend from relatively long attachment members 66 which extend from ring 63. Attachment members 66 may be provided with transverse ears 67 near syringe interface members 64. Release mechanism 62 may be made of any suitably sturdy material, such as but not limited to, stainless steel.

The action of release mechanism 62 and the operation of needle protector device 60 may be similar to that described hereinabove for needle protector device 10. That is, upon distal pushing of plunger 16, head 20 of plunger 16 contacts and distally pushes syringe interface members 64 of release mechanism 62. This may cause fingers 65 to move tongues 34 of protector tube 30 out of engagement with depressions 46 of outer tube 40, thereby permitting biasing device 50 to urge protector tube 30 distally to cover needle tip 26.

Figure 9:
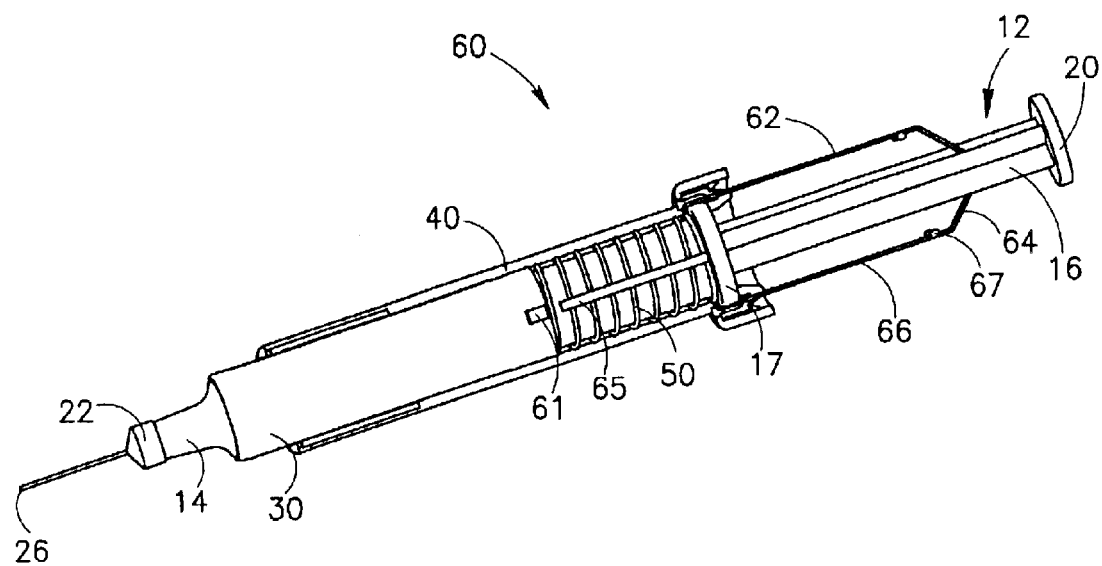
FIG. 9 is a simplified sectional illustration of a needle protector device for use with a hypodermic needle assembly, constructed and operative in accordance with another embodiment of the present invention.
Figure 10:
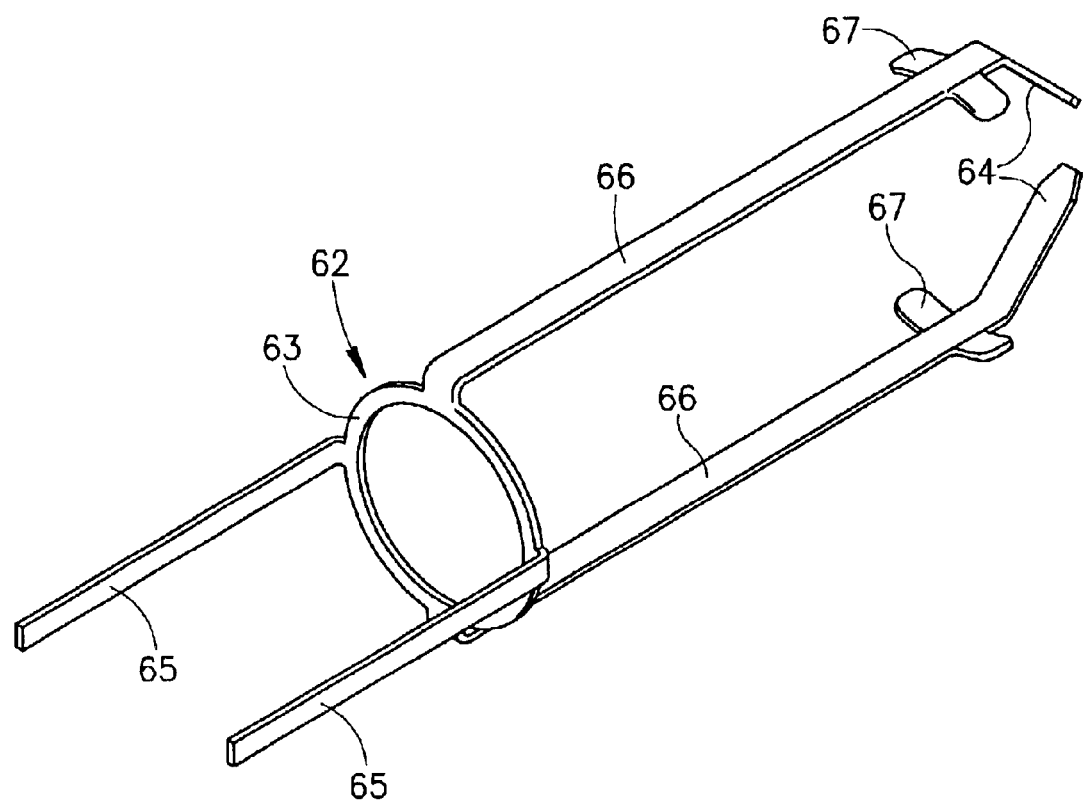
FIG. 10 is a more detailed illustration of a release mechanism of the needle protector device of FIG. 9.
Figure 11:
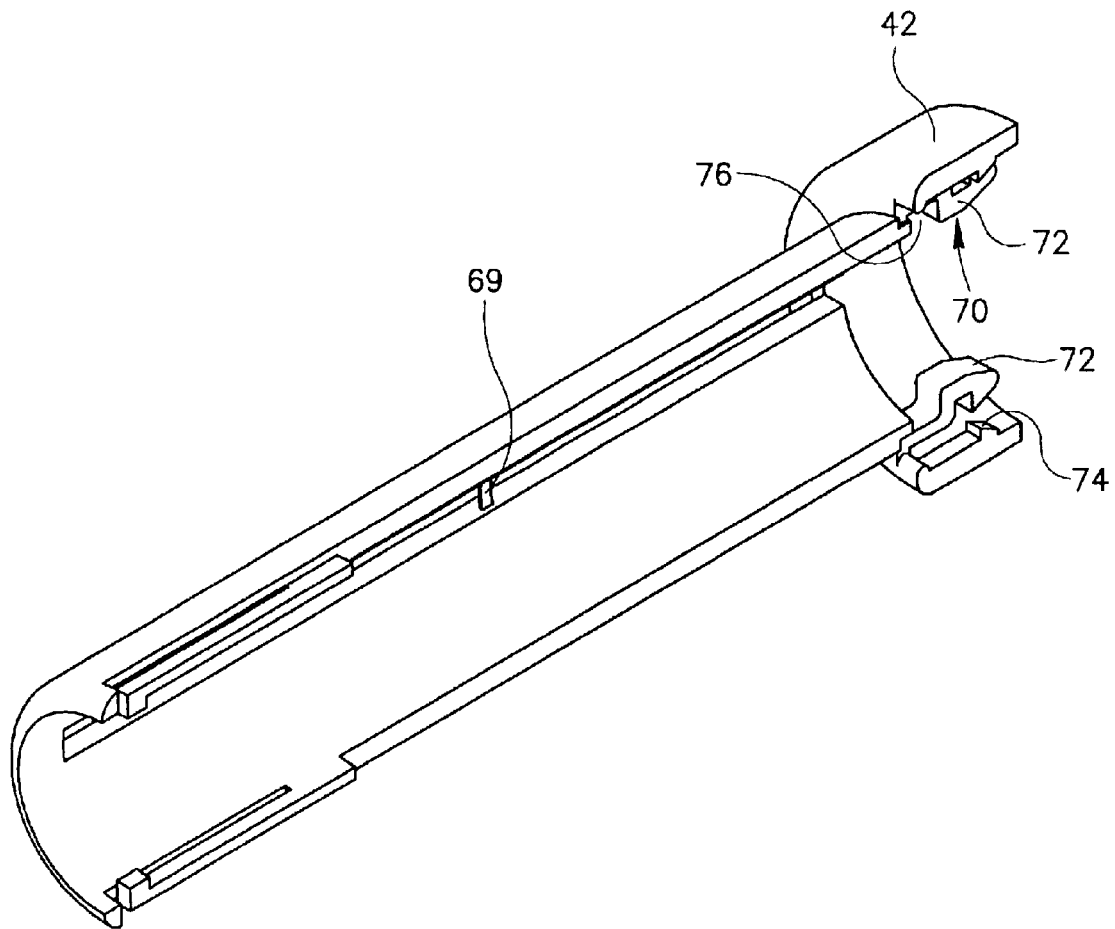
FIG. 11 is a pictorial illustration of a syringe holding device of the needle protector device of FIG. 9.

The embodiment illustrated in FIGS. 9 and 11, however, has a different trigger mechanism that releases protector tube 30 and permitting biasing device 50 to urge protector tube 30 distally to cover needle tip 26. In this embodiment, protector tube 30 comprises one or more outer abutments 61 (FIG. 9), which initially are proximal to one or more retaining stubs 69 (FIG. 11) formed in outer tube 40. Retaining stubs 69 may be configured to easily yield, break, rupture or shear. The trigger release action of this embodiment may be as follows. Upon distal pushing of plunger 16, head 20 of plunger 16 contacts and distally pushes syringe interface members 64 of release mechanism 62. This may cause fingers 65 to push outer abutments 61 against retaining stubs 69, whereupon outer abutments 61 shear retaining stubs 69. Once retaining stubs 69 are sheared, biasing device 50 may urge protector tube 30 distally to cover needle tip 26.

In needle protector device 60, in contrast with needle protector device 10, the biasing device 50 may not have to be initially in a contracted state. Instead, due to the long attachment members 66, release mechanism 62 contracts biasing device 50 upon distal pushing of plunger head 20, prior to fingers 65 triggering release of protector tube 30. By the time fingers 65 do release protector tube 30, biasing device 50 has sufficiently contracted to store the potential energy necessary for urging and propelling protector tube 30 distally to cover needle tip 26.

Another feature of needle protector device 60 that is not present in the embodiment of needle protector device 10 is a syringe holding device 70, seen best in FIG. 11 to which reference is now made. Syringe holding device 70 may comprise one or more resilient dogs 72 that face the proximal end of enlarged end 42, and chamfered protrusions 74 protruding from enlarged end 42, whose chamfered edges also faces the proximal end of enlarged end 42. The proximal hub 17 of syringe 14 (FIG. 9) may fit snugly in a notch 76 (FIG. 11) formed in resilient dogs 72.

Figure 12:
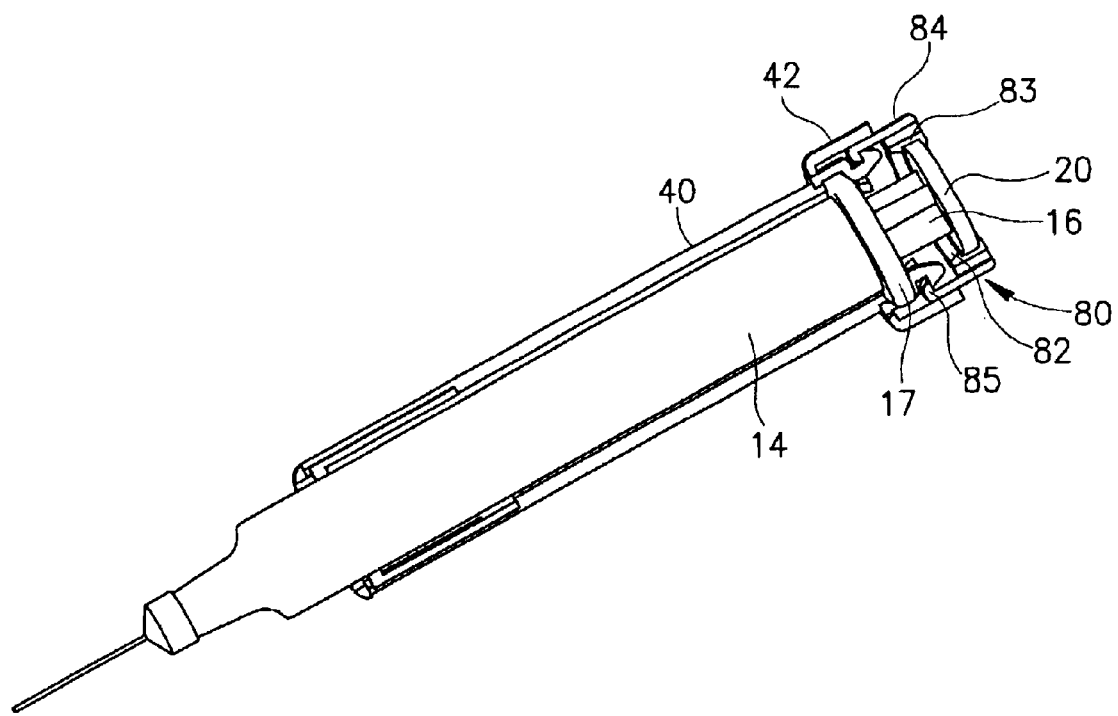
FIGS. 12 and 13 are pictorial illustrations of a plunger head holding device of the needle protector device of FIG. 9, respectively after and prior to fixedly holding the plunger head.
Figure 13:
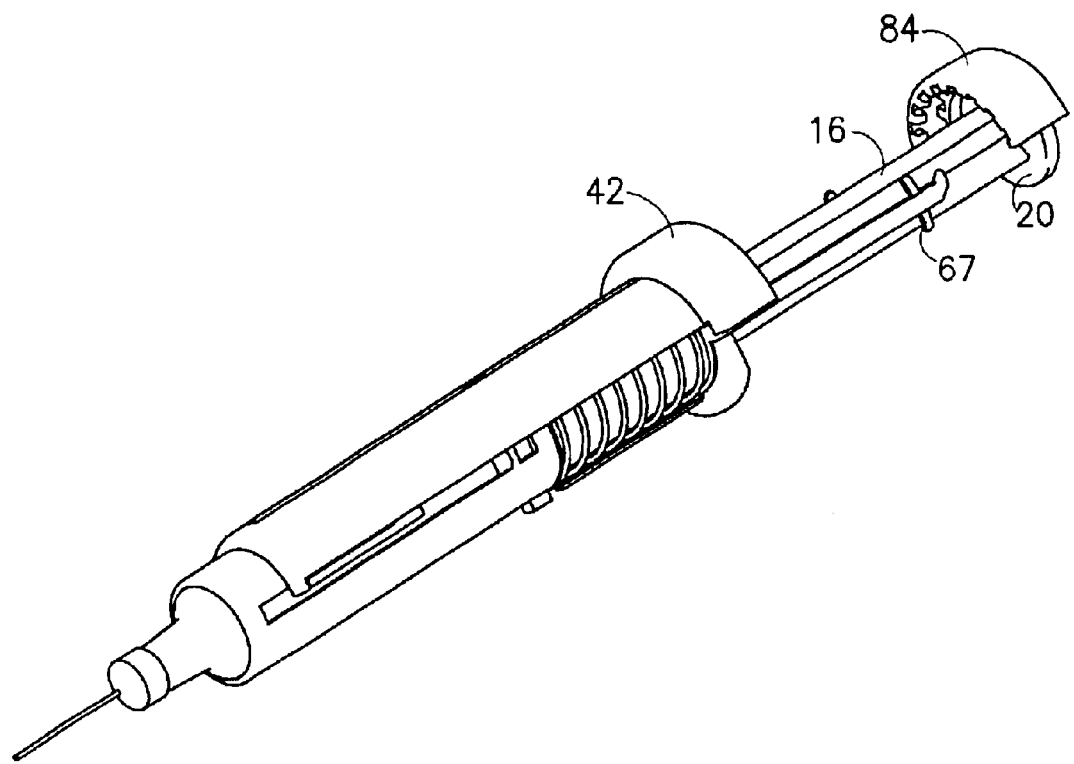

Reference is now made to FIGS. 12 and 13. In addition to syringe holding device 70, a plunger head holding device 80 may be provided. Plunger head holding device 80 may comprise one or more chamfered lugs 82 formed with a groove 83 in which the head 20 of plunger 16 may be fixedly received, such as by snap fit. A cap member 84 may distally extend from the outer periphery of lugs 82 and terminate in a plurality of catches 85 that face radially inwards. As seen in FIG. 12, after plunger head 20 has been pushed distally towards proximal hub 17 of syringe 14, catches 85 hook together with dogs 72. Plunger head 20 is now trapped and fixedly held, thereby safely preventing further use of syringe 14. In this trapped orientation, transverse ears 67 may snappingly lock on to chamfered protrusions 74 of enlarged end 42 so as to arrest movement of release mechanism 62 and thus reliably prevent inadvertent movement of protector tube 30 after removal of the needle from the patient's skin.

Figure 14:
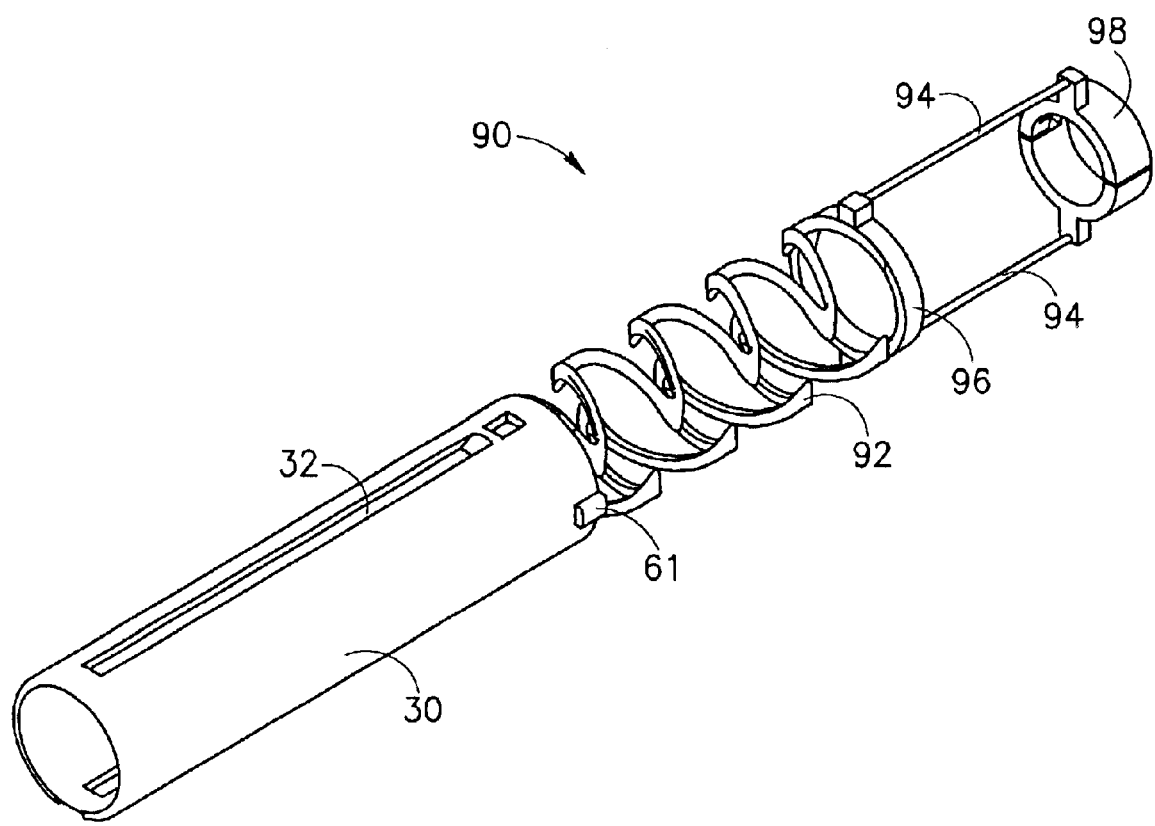
FIG. 14 is a simplified sectional illustration of a needle protector device for use with a hypodermic needle assembly, constructed and operative in accordance with yet another embodiment of the present invention.

Reference is now made to FIG. 14, which illustrates a needle protector device 90 for use with hypodermic needle assembly 12, constructed and operative in accordance with yet another embodiment of the present invention. Needle protector device 90 may comprise a biasing device 92 which is an integral extension of protector tube 30. Biasing device 92 may comprise a spiral spring molded of plastic together with protector tube 30. One or more proximally extending arms 94 may extend from an end ring 96 of biasing device 92. A clamping ring 98 may be attached to the proximal end of arms 94, and may be used to clamp on head 20 of syringe 14 (not shown in FIG. 14).

In the embodiment of FIG. 14, the trigger mechanism that releases protector tube 30 and permits biasing device 92 to urge protector tube 30 distally to cover needle tip 26 (not shown in FIG. 14), may be similar to that described hereinabove for the embodiment illustrated in FIGS. 9 and 11. That is, the outer abutments 61 of protector tube 30 may be initially proximal to retaining stubs 69 (FIG. 11) formed in outer tube 40. Upon distal pushing of plunger 16, outer abutments 61 push against and eventually shear retaining stubs 69. Once retaining stubs 69 are sheared, biasing device 92 may urge protector tube 30 distally to cover needle tip 26. It is noted that biasing device 92 may not have to be initially in a contracted state. Instead, by the time outer abutments 61 shear retaining stubs 69, biasing device 92 has sufficiently contracted to store the potential energy necessary for urging and propelling protector tube 30 distally to cover needle tip 26.

Any of the embodiments of the present invention may be used in conjunction with the AUTOJECT2 brand for COPAXONE® (glatiramer acetate injection) Pre-Filled Syringes, commercially available from Teva Pharmaceutical Industries Ltd., Israel.

It will be appreciated by person skilled in the art that the present invention is not limited by what has been particularly shown and described herein above. Rather the scope of the present invention is defined only by the claims that follow:

What is claimed is:

1. A needle protector device comprising:
   a protector tube slidingly disposed in an outer tube and slidingly disposed over a syringe comprising a needle, said protector tube comprising at least one abutment initially in engagement with said outer tube such that said protector tube is constrained from moving distally with respect to said syringe;
   a biasing device disposed inside said outer tube operative to provide an urging force on said protector tube in a direction that tends to urge said protector tube distally towards a tip of said needle; and
   a release mechanism operative to move said at least one abutment out of engagement with said outer tube upon distal pushing of a plunger of said syringe such that when said at least one abutment is out of engagement with said outer tube, said biasing device urges said protector tube distally towards the tip of said needle;
   wherein said at least one abutment comprises at least one resilient tongue that tends to spring radially outwards from an outer contour of said protector tube, and wherein said protector tube is formed with an elongate axial groove and a depression formed proximal to said groove, and said outer tube is formed with an elongate axial groove and a depression formed proximal to said groove, and at least one resilient tongue formed at a distal end thereof comprising lugs, wherein a proximal end of said at least one resilient tongue of said protector tube is initially fixedly received in said depression of said outer tube, and said lugs are initially received in said axial groove of said protector tube.

2. The needle protector device according to claim 1, wherein said depression of said protector tube is axially aligned with said groove of said protector tube.

3. The needle protector device according to claim 1, wherein said axial groove and said depression of said protector tube are formed through a wall thickness of said protector tube.

4. The needle protector device according to claim 1, wherein said axial groove of said protector tube is formed with a chamfered, proximal ramp.

5. The needle protector device according to claim 1, wherein said depression of said outer tube is axially aligned with said groove of said outer tube.

6. The needle protector device according to claim 1, wherein said axial groove and said depression of said outer tube are formed through a wall thickness of said outer tube.

7. A needle protector device comprising:
   a protector tube slidingly disposed in an outer tube and slidingly disposed over a syringe comprising a needle, said protector tube comprising at least one abutment initially in engagement with said outer tube such that said protector tube is constrained from moving distally with respect to said syringe;
   a biasing device disposed inside said outer tube operative to provide an urging force on said protector tube in a direction that tends to urge said protector tube distally towards a tip of said needle; and
   a release mechanism operative to move said at least one abutment out of engagement with said outer tube upon distal pushing of a plunger of said syringe, such that when said at least one abutment is out of engagement with said outer tube, said biasing device urges said protector tube distally towards the tip of said needle;
   and a cap member that receives therein a head of said plunger of said syringe, said cap member being arranged to lock on to a portion of said outer tube upon sufficient distal pushing of said plunger of said syringe so as to arrest movement of said plunger.

8. A needle protector device comprising:
   a protector tube slidingly disposed over a syringe comprising a needle, said protector tube being initially constrained from moving distally with respect to said syringe;
   a biasing device operative to provide an urging force on said protector tube in a direction that tends to urge said protector tube distally towards a tip of said needle; and
   a release mechanism operative to release and permit movement of said protector tube upon distal pushing of a plunger of said syringe, such that when said protector tube is released, said biasing device urges said protector tube distally towards the tip of said needle and said biasing device does not move reach the tip of said needle;
   wherein said protector tube is slidingly disposed in an outer tube;
   wherein said protector tube comprises at least one abutment initially in engagement with said outer tube such that said protector tube is constrained from moving distally with respect to said syringe; and wherein said protector tube is formed with an elongate axial groove and a depression formed proximal to said groove, and said outer tube is formed with an elongate axial groove and a depression formed proximal to said groove, and at least one resilient tongue formed at a distal end thereof comprising lugs, wherein a proximal end of said at least one resilient tongue of said protector tube is initially fixedly received in said depression of said outer tube, and said lugs are initially received in said axial groove of said protector tube.

* * * * *